United States Patent
Ishida (10) Patent No.: US 12,036,372 B2
(45) Date of Patent: Jul. 16, 2024

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 500 days.

(21) Appl. No.: 17/193,228

(22) Filed: Mar. 5, 2021

(65) Prior Publication Data

US 2021/0187245 A1 Jun. 24, 2021

Related U.S. Application Data

(63) Continuation of application No. PCT/JP2019/032403, filed on Aug. 20, 2019.

(30) Foreign Application Priority Data

Sep. 12, 2018 (JP) .................. 2018-170580

(51) Int. Cl.
*A61M 25/01* (2006.01)
*A61L 29/04* (2006.01)
(Continued)

(52) U.S. Cl.
CPC ....... *A61M 25/0141* (2013.01); *A61L 29/042* (2013.01); *A61L 29/049* (2013.01);
(Continued)

(58) Field of Classification Search
CPC .............. A61M 25/0141; A61M 25/06; A61M 25/0606; A61M 25/008; A61M 25/0054;
(Continued)

(56) References Cited

U.S. PATENT DOCUMENTS 4,402,684 A * 9/1983 Jessup ............... A61M 25/0102
128/207.14
4,563,181 A * 1/1986 Wijayarathna ...... A61M 25/008
600/433
(Continued)

FOREIGN PATENT DOCUMENTS

CN 106236213 A * 12/2016
CN 108057167 A * 5/2018
(Continued)

OTHER PUBLICATIONS

International Searching Authority, "Written Opinion," issued in connection with PCT Patent Application No. PCT/JP2019/032403, dated Oct. 1, 2019.
(Continued)

*Primary Examiner* — Jason E Flick
*Assistant Examiner* — Adam J. Cermak
(74) *Attorney, Agent, or Firm* — Foley & Lardner LLP (57) ABSTRACT

A catheter assembly includes a catheter and an inner needle. The catheter has a catheter body and a flexible portion that is provided on a distal portion of the catheter body, includes a distal-most portion of the catheter, and is more flexible than the catheter body. The catheter body is made of a first material. The flexible portion is made of a second material. A change in flexibility of the second material between 25° C. and 37° C. is smaller than a change in flexibility of the first material between 25° C. and 37° C.

16 Claims, 9 Drawing Sheets

(51) Int. Cl.
*A61M 25/00* (2006.01)
*A61M 25/06* (2006.01)
(52) U.S. Cl.
CPC ...... *A61M 25/007* (2013.01); *A61M 25/0097* (2013.01); *A61M 25/06* (2013.01)
(58) Field of Classification Search
CPC ... A61M 2205/0216; A61M 2025/0081; A61L 29/042; A61L 29/049
See application file for complete search history.

(56) References Cited

U.S. PATENT DOCUMENTS

| | | | | |
|---|---|---|---|---|
| 5,017,259 | A * | 5/1991 | Kohsai | B29C 57/00 264/248 |
| 5,234,416 | A * | 8/1993 | Macaulay | A61M 25/0068 600/437 |
| 5,762,630 | A * | 6/1998 | Bley | A61L 29/14 604/524 |
| 5,957,966 | A * | 9/1999 | Schroeppel | A61N 1/056 607/128 |
| 5,997,526 | A * | 12/1999 | Giba | A61M 25/0041 607/125 |
| 6,001,078 | A * | 12/1999 | Reekers | A61M 25/0068 604/35 |
| 6,002,969 | A * | 12/1999 | Machek | A61N 1/0573 607/122 |
| 6,221,050 | B1 * | 4/2001 | Ishida | A61M 25/0606 604/167.03 |
| 6,245,053 | B1 * | 6/2001 | Benjamin | A61M 25/0014 604/524 |
| 6,325,790 | B1 * | 12/2001 | Trotta | A61L 29/049 600/433 |
| 6,610,046 | B1 * | 8/2003 | Usami | A61M 25/09 600/585 |
| 6,719,749 | B1 * | 4/2004 | Schweikert | A61M 25/0009 604/28 |
| 6,893,427 | B1 * | 5/2005 | Jimenez | A61M 25/0043 604/525 |
| 8,945,058 | B2 * | 2/2015 | Pravongviengkham | A61B 17/3494 604/164.01 |
| 10,213,578 | B2 * | 2/2019 | Fukuoka | A61M 25/0069 |
| 2002/0010417 | A1 * | 1/2002 | Bertram | A61M 16/0445 604/96.01 |
| 2003/0153898 | A1 * | 8/2003 | Schon | A61M 25/0026 604/544 |
| 2010/0030165 | A1 * | 2/2010 | Takagi | A61L 29/085 604/525 |
| 2013/0066276 | A1 * | 3/2013 | Ito | A61M 5/158 604/164.08 |
| 2014/0114290 | A1 * | 4/2014 | Okamura | A61M 25/0662 604/528 |
| 2015/0231360 | A1 * | 8/2015 | Watanabe | A61M 25/0021 604/523 |
| 2015/0265802 | A1 * | 9/2015 | Fukuoka | A61M 25/0069 604/523 |
| 2016/0129221 | A1 * | 5/2016 | Haverkost | A61M 25/0068 604/524 |
| 2016/0310704 | A1 * | 10/2016 | Ng | A61M 25/0009 |
| 2018/0015254 | A1 * | 1/2018 | Cragg | A61M 25/0108 |
| 2023/0047163 | A1 * | 2/2023 | Tal | A61M 25/0054 |

FOREIGN PATENT DOCUMENTS

| | | | | |
|---|---|---|---|---|
| JP | H02-191466 | A | | 7/1990 |
| JP | H04-108554 | U | | 9/1992 |
| JP | 08112343 | A | * | 5/1996 |
| JP | H08-112343 | A | | 5/1996 |
| JP | 2002-143329 | A | | 5/2002 |
| JP | 2008-043445 | A | | 2/2008 |
| JP | 2011-251081 | A | | 12/2011 |
| WO | WO-9505862 | A1 * | 3/1995 | ........ A61M 25/0068 |
| WO | WO-2015146408 | A1 * | 10/2015 | ............ A61F 2/958 |

OTHER PUBLICATIONS

Office Action issued in connection with Japanese Appl. No. 2020-546795 dated Sep. 12, 2023.

International Searching Authority, "International Search Report," issued in connection with International Patent Application No. PCT/JP2019/032403, dated Oct. 1, 2019.

\* cited by examiner

CATHETER ASSEMBLY

CROSS-REFERENCE TO RELATED APPLICATIONS

This application is a bypass continuation of PCT Application No. PCT/JP2019/032403, filed on Aug. 20, 2019, which claims priority to Japanese Application No. 2018-170580, filed on Sep. 12, 2018. The contents of these applications are hereby incorporated by reference in their entireties.

BACKGROUND

The present disclosure relates to a catheter assembly configured to be punctured and be indwelled in a blood vessel when performing an infusion or the like to a patient, for example.

Conventionally, a catheter assembly used when performing an infusion or the like to a patient has been known. This kind of the catheter assembly includes a hollow catheter, a catheter hub fixed to a proximal end of the catheter, a hollow inner needle that is inserted into the catheter and has a sharp needle tip at a distal end, and a needle hub fixed to a proximal end of the inner needle (for example, see JP 2008-43445 A). When using a catheter assembly, a skin and a blood vessel of a living body are punctured with each distal end of the inner needle and the catheter, and then, the catheter is advanced with respect to the inner needle so that the catheter is inserted into the blood vessel by a predetermined length.

SUMMARY

In a conventional catheter assembly having an inner needle and a catheter, a catheter distal end is sometimes caught by a blood vessel back wall (a blood vessel wall opposing a puncture spot) when a puncture angle is large. As a result, the catheter is hardly inserted into a blood vessel or the blood vessel wall is damaged by the catheter distal end. Certain embodiments of the present invention have been developed in consideration of such a problem, and an object thereof is to provide a catheter assembly capable of preventing a catheter distal end from being caught by a blood vessel back wall at the time of advancing a catheter to a blood vessel even when a puncture angle, which is the angle between a central axis of the blood vessel to be punctured and a central axis of an inner needle with which the puncture is performed, is large.

One aspect of the present invention is a catheter assembly including a catheter and an inner needle inserted through the catheter. The catheter has a catheter body and a flexible portion that is provided on a distal portion of the catheter body, includes a distal-most portion of the catheter, and is more flexible than the catheter body. The catheter body is made of a first material, and the flexible portion is made of a second material. A change in flexibility of the second material between 25° C. and 37° C. is smaller than a change in flexibility of the first material between 25° C. and 37° C.

According to the catheter assembly of the present invention, the flexible portion, which is more flexible than the catheter body, is provided at the distal portion of the catheter body, and thus, it is possible to prevent a distal end of the catheter from being caught by a blood vessel back wall even when a puncture angle is large. Accordingly, it is possible to prevent the catheter from being hardly inserted into a blood vessel or to prevent a blood vessel wall from being damaged by the catheter distal end. Because the change in flexibility of the second material between 25° C. and 37° C. forming the flexible portion is smaller than the change in flexibility of the first material between 25° C. and 37° C. forming the catheter body, the distal end of the catheter is soft, and thus, hardly damages the blood vessel, and the catheter body is hard, and thus, is easily inserted when a catheter is inserted into a living body. After the catheter is indwelled, the flexible portion constituting the distal end of the catheter is not as soft as compared with the time of insertion, and thus, the flexible portion is hardly crushed during blood suction. On the other hand, after the catheter is indwelled, the catheter body softens due to the body temperature as compared with the time of insertion and adapts to a shape of the blood vessel, and thus, the stimulation to the blood vessel is reduced.

DETAILED DESCRIPTION

Hereinafter, embodiments of a catheter assembly according to the present invention will be described with reference to the accompanying drawings.

Figure 1:
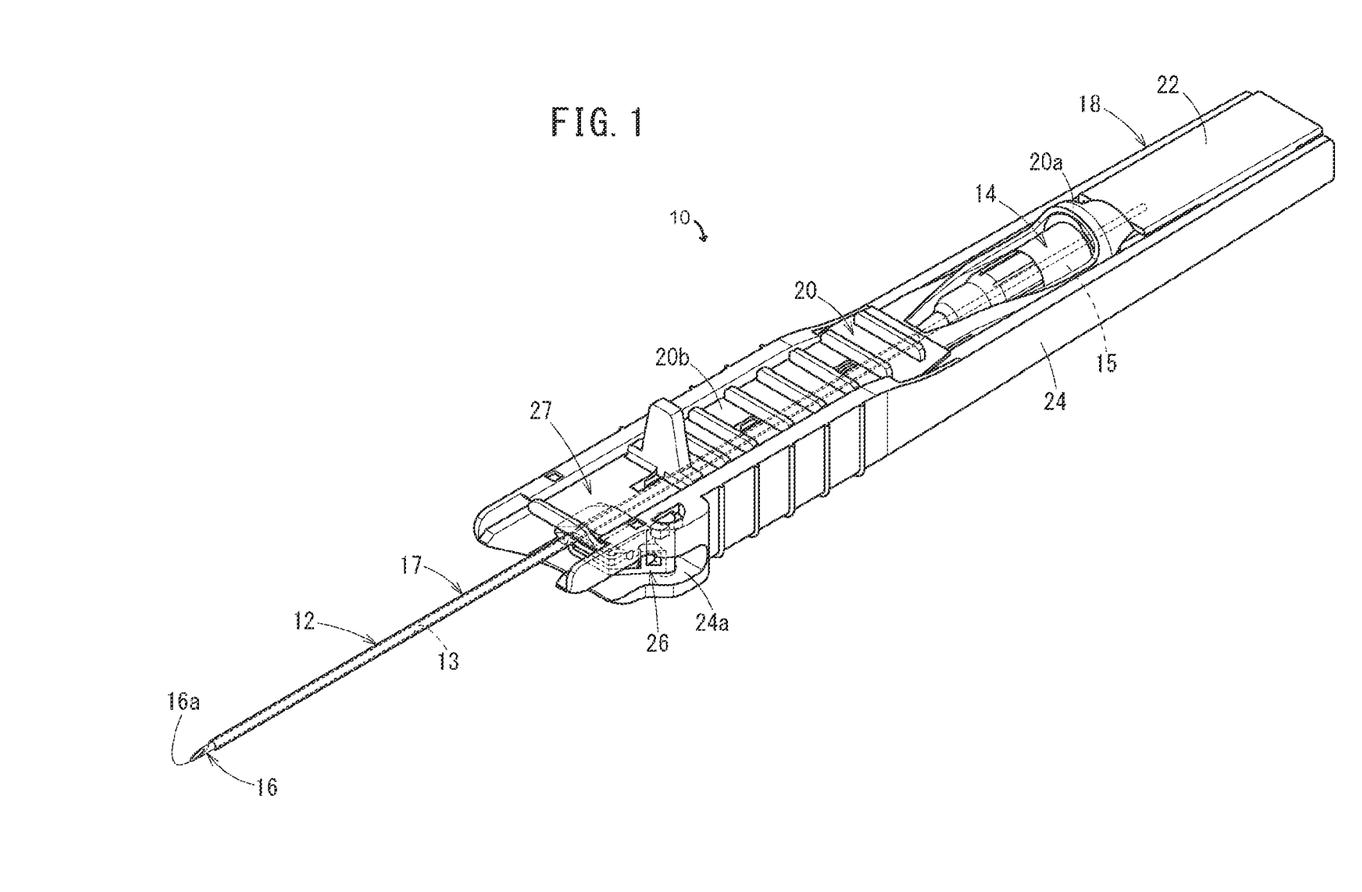
FIG. 1 is a perspective view of a catheter assembly according to an embodiment of the present invention.

The catheter assembly 10 whose initial state is illustrated in FIG. 1 is applied when performing an infusion, a blood transfusion, and the like to a patient (living body), and forms an introduction portion for a medicinal liquid or the like by being punctured into the patient's body to be indwelled. The catheter assembly 10 may be configured as a catheter having a longer length (for example, a central venous catheter, a PICC, a mid-line catheter, and the like) than a peripheral venous catheter. Incidentally, the catheter assembly 10 may be configured as the peripheral venous catheter. In addition, the catheter assembly 10 is not limited to the venous catheter, and may be configured as an arterial catheter such as a peripheral arterial catheter.

As illustrated in FIG. 1, the catheter assembly 10 includes a catheter 12, a catheter hub 14 fixedly holding the catheter 12, a hollow inner needle 16 removably inserted into the catheter 12, a needle hub 18 fixedly holding the inner needle 16, and a catheter operation member 20 mounted to the catheter hub 14. The inner needle 16 may be a solid needle.

The catheter assembly 10 forms a multi-tube structure (multi-tube portion) in which the catheter 12 and the inner needle 16 are sequentially stacked in an initial state before use.

The catheter 12 is flexible and has a lumen 13 formed to penetrate therethrough. The lumen 13 is formed to have a diameter capable of accommodating the inner needle 16 and capable of causing a medicinal liquid, blood, or the like to flow. A distal end of the catheter 12 is reduced in diameter in order to decrease a puncture resistance, and an inner surface of the catheter 12 is in close contact with an outer surface of the inner needle 16 at such a reduced diameter portion in the initial state of the catheter assembly 10. A length of the catheter 12 is not particularly limited but can be appropriately designed according to use and various conditions, and is set to, for example, about 14 to 500 mm, about 30 to 400 mm, or about 76 to 200 mm.

A proximal portion of the catheter 12 is fixed to a distal portion inside the catheter hub 14. The catheter 12 and the catheter hub 14 form a catheter member 17.

The catheter hub 14 is exposed on the patient's skin in a state in which the catheter 12 has been inserted into a blood vessel, and indwelled together with the catheter 12 by being pasted with a tape or the like. The catheter hub 14 is formed in a tubular shape tapered in a distal direction.

A constituent material of the catheter hub 14 is not particularly limited, but a thermoplastic resin, such as polypropylene, polycarbonate, polyamide, polysulfone, polyarylate, a methacrylate-butylene-styrene copolymer, and polyurethane may be preferably applied.

A hollow portion 15 that communicates with the lumen 13 of the catheter 12 and through which an infusion solution can flow is provided inside the catheter hub 14. A hemostatic valve, a plug, or the like (not illustrated) may be accommodated inside the hollow portion 15 in order to prevent back-flow of blood at the time of puncture with the inner needle 16 and to allow infusion along with insertion of a connector of an infusion tube.

The inner needle 16 is configured as a hollow tube having rigidity that enables puncture of a skin of a living body, and is arranged to penetrate through the lumen 13 of the catheter 12 and the hollow portion 15 of the catheter hub 14. The inner needle 16 is formed to have a total length longer than that of the catheter 12, and a sharp needle tip 16a is provided at a distal end thereof. A lumen penetrating in an axial direction of the inner needle 16 is provided inside the inner needle 16, and this lumen communicates with a distal opening of the inner needle 16.

Examples of a constituent material of the inner needle 16 include a metal material such as stainless steel, aluminum or an aluminum alloy, and titanium or a titanium alloy, a hard resin, ceramics, and the like.

The needle hub 18 has a needle holding member 22 fixed to a proximal portion of the inner needle 16, and a housing 24 to which the needle holding member 22 is fixed and that extends along the inner needle 16 and the catheter 12. The catheter assembly 10 accommodates a part of the multi-tube portion, the catheter hub 14, and the catheter operation member 20 in the housing 24 in the initial state. Resin materials forming the needle holding member 22 and the housing 24 are not particularly limited, but, for example, the materials exemplified for the catheter hub 14 can be appropriately selected. Incidentally, the needle holding member 22 and the housing 24 may be integrally formed.

When the needle hub 18 is moved to a proximal direction with respect to the catheter 12, the inner needle 16 is also moved in the proximal direction with respect to the catheter 12 along with the movement of the needle hub 18 because the needle hub 18 holds the inner needle 16 at the needle holding member 22.

The catheter operation member 20 is attached to the catheter hub 14. Thus, when the catheter operation member 20 is advanced relative to the needle hub 18, the catheter member 17 is advanced relative to the inner needle 16. The catheter operation member 20 has a hub mounting portion 20a detachably mounted on the catheter hub 14, and an operation plate portion 20b extending from the hub mounting portion 20a along the catheter 12 in the distal direction. Incidentally, the catheter operation member 20 is not necessarily provided in the catheter assembly 10.

The catheter assembly 10 is provided with a support member 26 on the distal side of the housing 24 in order to support a lower side of the catheter 12 held by the catheter operation member 20. The support member 26 is rotatably attached to an arrangement concave portion 24a provided at a distal portion of the housing 24. A distal portion of the catheter operation member 20 and the support member 26 constitute a deflection suppressing mechanism 27.

When the skin is punctured with the inner needle 16 and the catheter 12, the distal portion of the catheter operation member 20 supports the catheter 12 from above and the support member 26 supports the catheter 12 from below, and thus, deflections of the catheter 12 and the inner needle 16 are suppressed. When the catheter operation member 20 is removed out of the housing 24, the support member 26 is rotated toward an outer side of the housing 24 by being pushed by the hub mounting portion 20a, and thus, the catheter hub 14 can be withdrawn from the housing 24 in the distal direction. Incidentally, the support member 26 is not necessarily provided.

Figure 2:
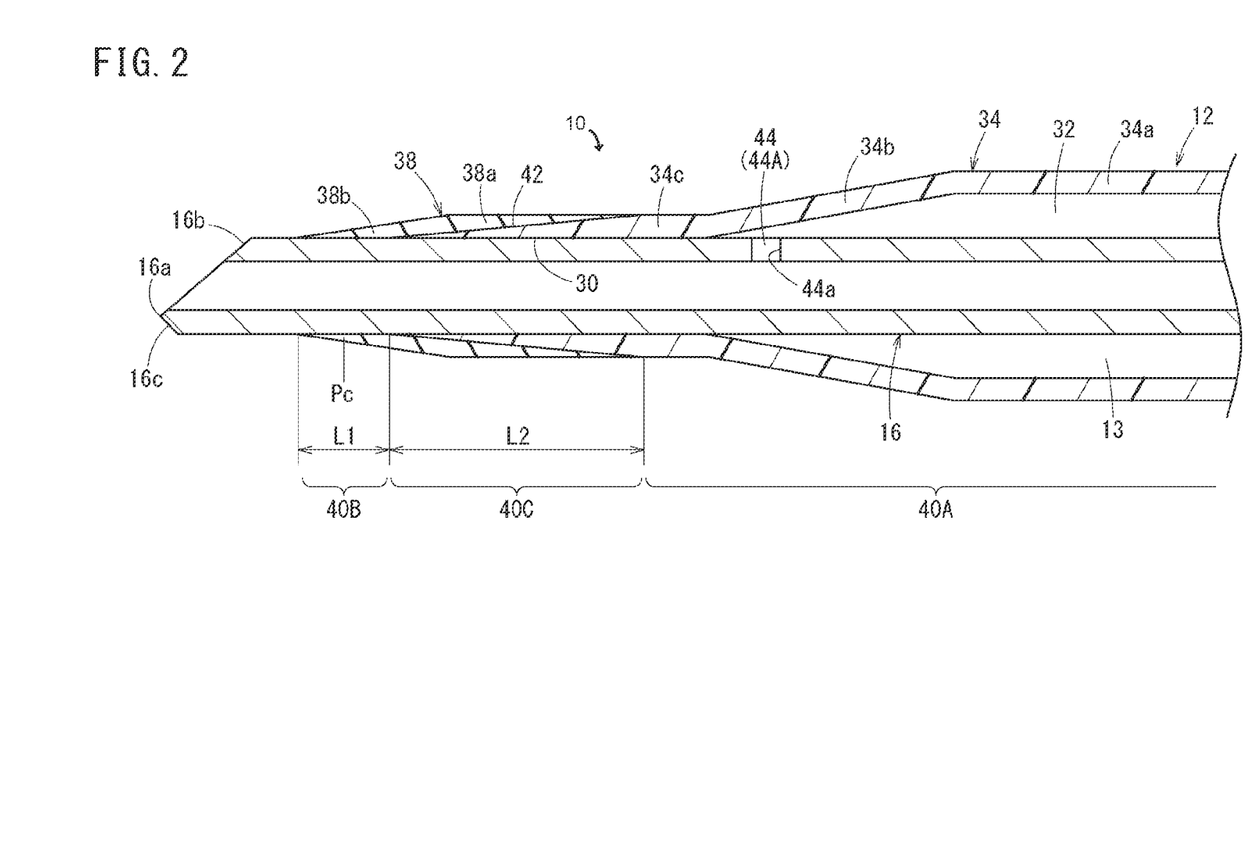
FIG. 2 is a cross-sectional view of a distal portion of the catheter assembly.

As illustrated to FIG. 2, the catheter 12 has a close contact portion 30, which is in close contact with an outer circumferential surface of the inner needle 16, in at least a part of an inner circumferential surface. The close contact portion 30 is provided on the inner circumferential surface of a distal portion of the catheter 12. A flow path for flashback confirmation (hereinafter, referred to as "flashback flow path 32") is formed between the catheter 12 and the inner needle 16 on the proximal side of the close contact portion 30. The flashback flow path 32 extends up to a proximal opening of the catheter 12.

The catheter 12 has a catheter body 34 that constitutes a main portion of the catheter 12 and a flexible portion 38 provided at a distal portion of the catheter body 34. Thus, the catheter 12 becomes more flexible toward the distal-most portion on the distal side. The flexible portion 38 is exposed from the housing 24 (FIG. 1).

The catheter body 34 accounts for most of the whole length of the catheter 12. Thus, the distal-most portion of the catheter body 34 is positioned near the distal-most end of the catheter 12. The catheter 12 and the flexible portion 38 are made of a resin material having flexibility. A creep strain of the catheter body 34 is greater than a creep strain of the flexible portion 38.

The catheter body 34 has: a straight portion 34a that has a constant outer diameter along the axial direction; a tapered portion 34b that extends from the straight portion 34a in the distal direction and has an outer diameter decreasing in the distal direction; and a distal constituting portion 34c that extends from the tapered portion 34b in the distal direction and constitutes a portion up to the distal-most portion of the catheter body 34. An inner circumferential surface of the distal constituting portion 34c is in close contact with (fitted to) the inner needle 16 in a liquid-tight manner over the whole outer circumferential surface.

The flashback flow path 32 is formed between an inner circumferential surface of the catheter body 34 (specifically, the straight portion 34a and the tapered portion 34b) and the outer circumferential surface of the inner needle 16. At least the catheter body 34 between the catheter body 34 and the flexible portion 38 has transparency such that a flashback can be confirmed.

The catheter 12 is supported by the support member 26 (FIG. 1) at a spot of the catheter body 34 (the catheter body 34 is supported by the support member 26). As a result, it is possible to reliably support the catheter 12 and to reduce a sliding resistance at the time of advancing the catheter 12. Moreover, the portion supported by the support member 26 (FIG. 1) is located on the proximal side of an interface 42 between the catheter body 34 and the flexible portion 38, and thus, it is possible to prevent peeling of the interface 42 caused by sliding of the catheter 12 with respect to the support member 26.

It is preferably that the catheter body 34 be less likely to swell as compared with the flexible portion 38. As a result, it is possible to set an axial distance between a most proximal position of a blade surface 16b of the inner needle 16 and a distal-most position of the catheter 12 to a desired size and to reduce a variation for each product during steam sterilization (autoclave sterilization) or ethylene oxide gas sterilization in a process of manufacturing the catheter assembly 10.

The catheter body 34 is made of a first material. Examples of a first material include a fluorine-based resin such as polytetrafluoroethylene (PTFE), an ethylene-tetrafluoroethylene copolymer (ETFE), and a perfluoroalkoxy fluorine resin (PFA), an olefin-based resin such as polyethylene and polypropylene or a mixture thereof, polyurethane, polyester, polyamide, a polyether nylon resin, a mixture of the olefin-based resin and an ethylene-vinyl acetate copolymer, and the like. A durometer hardness of the catheter body 34 is, for example, less than D70.

The flexible portion 38 includes the distal-most portion of the catheter 12. The flexible portion 38 is more flexible than the catheter body 34. That is, an elastic modulus k1 of the catheter body 34 and an elastic modulus k2 of the flexible portion 38 have a relationship of k1>k2.

The flexible portion 38 has a straight portion 38a that has a constant outer diameter along the axial direction, and a tapered portion 38b that extends from the straight portion 38a in the distal direction and has an outer diameter decreasing in the distal direction. An inner circumferential surface of the flexible portion 38 is in close contact with (fitted to) an outer circumferential surface of the inner needle 16 in a liquid-tight manner over the whole outer circumference.

It is preferable that at least the flexible portion 38 (among the catheter body 34 and the flexible portion 38) have an X-ray contrast property. As a result, for example, when the catheter 12 is broken in a blood vessel, it is possible to easily confirm a location of the catheter 12, which has been broken and left in the blood vessel, by X-ray. A contrast layer in the case where the flexible portion 38 has the contrast property may be provided, for example, in any form of a stripe shape, an intermediate layer in the radial direction, or the whole layer.

The flexible portion 38 is made of a second material. Examples of a second material include various rubber materials such as natural rubber, butyl rubber, isoprene rubber, butadiene rubber, styrene-butadiene rubber, silicone rubber, various thermoplastic elastomers such as polyurethanes, polyesters, polyamides, olefins, and styrenes or a mixture thereof, and the like.

A change in flexibility of the second material (constituent material of the flexible portion 38) between 25° C. and 37° C. is smaller than a change in flexibility of the first material (constituent material of the catheter body 34) between 25° C. and 37° C. Each change in flexibility can be recognized as a change in elastic modulus. For example, when the elastic modulus of the first material at 25° C. and 37° C. are H1a and H1b, respectively, a change (degree of change) in elastic modulus of the first material between 25° C. and 37° C. is H1a/H1b. When the elastic modulus of the second material at 25° C. and 37° C. are H2a and H2b, respectively, a change (degree of change) of the elastic modulus of the second material between 25° C. and 37° C. is H2a/H2b. Therefore, H2a/H2b<H1a/H1b is established.

Here, 25° C. is a typical temperature of room temperature. Further, 37° C. is a typical temperature of human body temperature. Both the first material and the second material have elastic modulus at 37° C. lower than elastic modulus at 25° C. That is, after the catheter 12 remains indwelled, the catheter body 34 and the flexible portion 38 are warmed to soften due to the body temperature, and become more flexible as compared with the time of inserting the catheter 12 into human (and the time before insertion). The first material and the second material may be of the same type having different hardness from each other. For example, even if the first material and the second material are of the same type, the above-described changes in elastic modulus with the temperature can be made different depending on an average molecular weight, a functional group, an additive, and the like.

In the catheter 12, a single catheter body region 40A where only the catheter body 34 between the catheter body 34 and the flexible portion 38 exists, a single flexible portion region 40B where only the flexible portion 38 between the catheter body 34 and the flexible portion 38 exists, and a mixed region 40C where the catheter body 34 and the flexible portion 38 exist are arranged in the axial direction. In the catheter 12 illustrated in FIG. 2, the interface 42 between the catheter body 34 and the flexible portion 38 is formed in a tapered shape that is inclined at a substantially constant angle with respect to an axis of the catheter 12.

The single catheter body region 40A is a portion of the catheter body 34 present on the proximal side of a most proximal portion of the flexible portion 38.

The single flexible portion region 40B is a portion of the flexible portion 38 present on the distal side of the distal-most portion of the catheter body 34. An axial length L1 of the single flexible portion region 40B is set to, for example, 0.3 to 5.0 mm, preferably 0.4 to 2.0 mm, and more preferably 0.5 to 0.9 mm. The hardness of the flexible portion (the single flexible portion region 40B) is, for example, A80 to D67 and preferably D53 to D64 at 23° C. The flexible portion 38 in the illustrated example is joined to the catheter body 34. Because the axial length L1 and the hardness of the single flexible portion region 40B are set within the above ranges, it is possible to prevent the distal end (the flexible portion 38) of the catheter 12 from being curled at the time of puncture. In addition, it is possible to preferably suppress catching by a blood vessel back wall 50a at the time of inserting the catheter 12. Further, it is possible to suppress crushing of the distal end of the catheter 12 at the time of suctioning blood.

The mixed region 40C is a portion in which the catheter body 34 and the flexible portion 38 are stacked in the radial direction. An axial length L2 of the mixed region 40C is set to, for example, 1 to 5 mm, and preferably 2 to 3 mm.

In the catheter 12 illustrated in FIG. 2, the interface 42 between the catheter body 34 and the flexible portion 38 is inclined in the distal direction so as to approach the axis (center) of the catheter 12. Thus, the flexible portion 38 is present on the outer side of the catheter body 34 in the mixed region 40C.

Instead of the above configuration having the interface 42, the catheter 12 may be formed so as to become soft in the distal direction by changing each compounding amount of materials different in hardness in the axial direction. In this case, extrusion molding may be performed while changing each extrusion speed of different materials. Alternatively, a content of a plasticizer at the distal portion of the catheter 12 may be increased. In this case, the plasticizer may be applied to the distal portion of the catheter 12.

In the inner needle 16, a backcut portion 16c, which is continuous with the needle tip 16a and is inclined in a reverse direction to the blade face 16b with respect to the axis of the inner needle 16, is provided on the opposite side to a blade face 16b.

Figure 3:
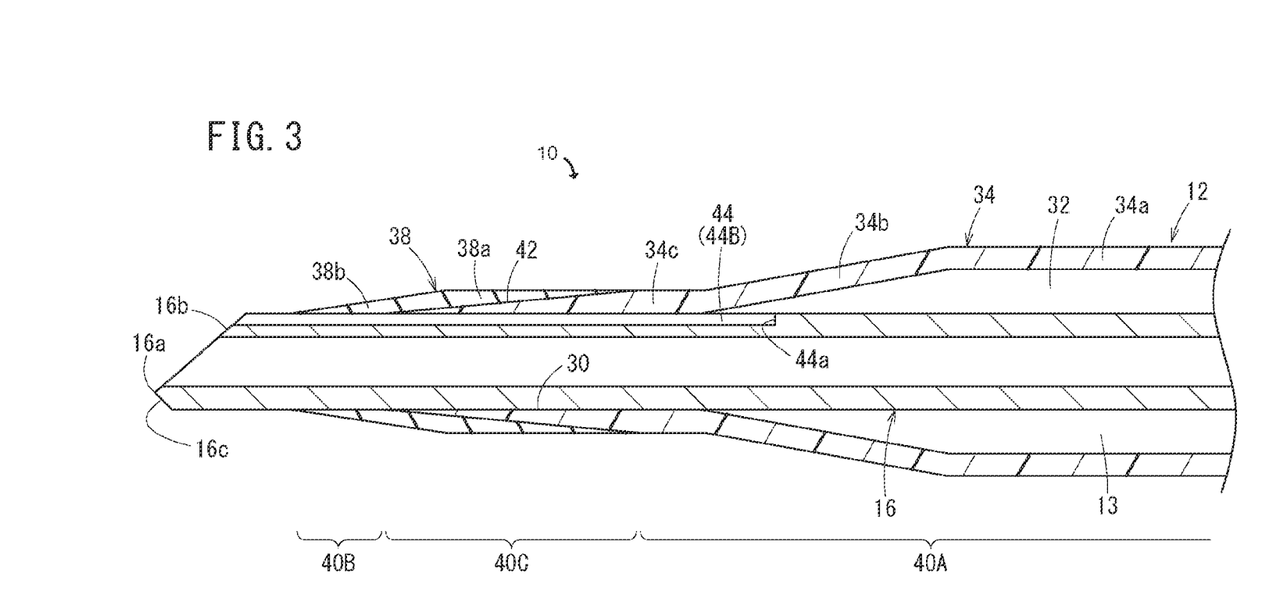
FIG. 3 is a cross-sectional view of a distal portion in another configuration of the catheter assembly.

The inner needle 16 is provided with an introduction path 44 that communicates with the flashback flow path 32 to introduce blood into the flashback flow path 32. The introduction path 44 illustrated in FIG. 2 is a side hole 44A that penetrates through a wall portion of the inner needle 16 in the radial direction. As illustrated in FIG. 3, the introduction path 44 may be a groove portion 44B extending in the axial direction on the outer circumferential surface of the inner needle 16.

In the initial state of the catheter assembly 10 illustrated in FIGS. 2 and 3, a proximal end 44a of the introduction path 44 is provided on the proximal side of an axial center position Pc of the single flexible portion region 40B. More specifically, at least the proximal end 44a of the introduction path 44 is provided on the proximal side of a distal-most portion of the single catheter body region 40A. The whole side hole 44A illustrated in FIG. 2 is provided on the proximal side of the distal-most portion of the single catheter body region 40A. Incidentally, a part of the side hole 44A may be present on the distal side of the distal-most portion of the single catheter body region 40A.

In FIG. 2, the whole side hole 44A is provided on the proximal side of the mixed region 40C. A part of the side hole 44A may be present on the distal side of a proximal end of the mixed region 40C.

Regarding a position of the introduction path 44 in relation to the close contact portion 30, at least the proximal end 44a of the introduction path 44 (the side hole 44A or the groove portion 44B) is provided on the proximal side of the close contact portion 30 in the initial state of the catheter assembly 10 illustrated in FIGS. 2 and 3. The whole side hole 44A illustrated in FIG. 2 is provided on the proximal side of the close contact portion 30.

Next, a procedure (method for inserting the catheter assembly 10) using the catheter assembly 10 configured as described above will be described.

Figure 4:
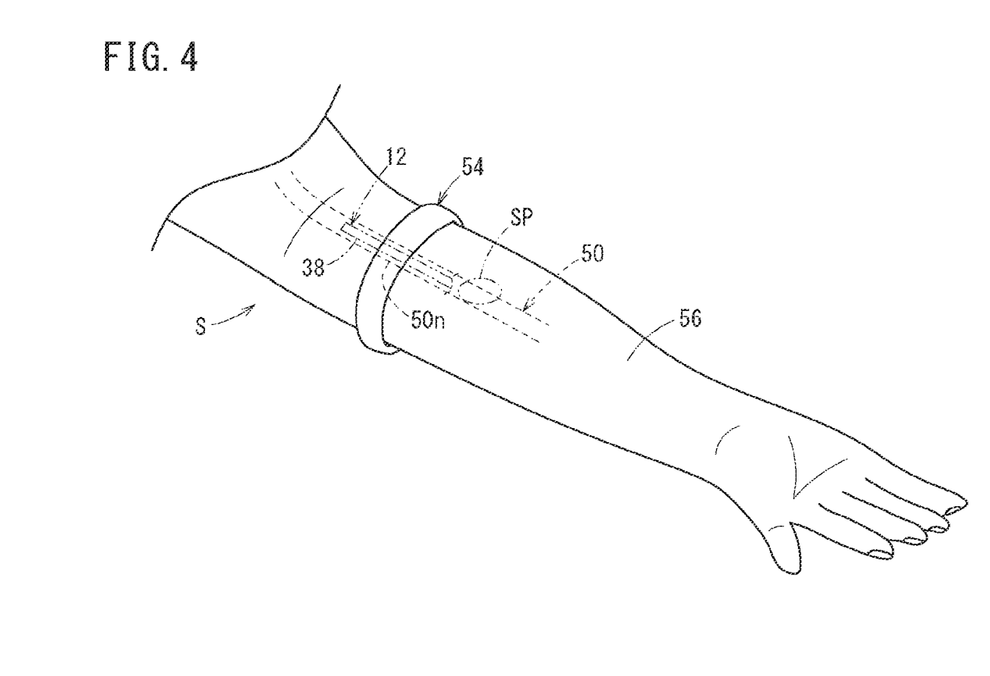
FIG. 4 is a first explanatory view of a procedure using the catheter assembly.

A puncturing operation of puncturing a patient's skin with the catheter assembly 10 is performed in the use of the catheter assembly 10 illustrated in FIG. 1. Prior to this puncturing operation, a tourniquet 54 is wrapped around a central side (side closer to the heart) of a planned puncture site SP in a part of the human body as illustrated in FIG. 4 (a tourniquet attachment step). At a spot wrapped with the tourniquet 54, a blood vessel 50 (vein) is compressed so that the blood vessel 50 is narrowed or collapses. The part of the human body illustrated in FIG. 4 is an arm 56 (specifically, forearm). In another aspect, the tourniquet 54 may be wrapped around an upper arm and the planned puncture site SP may be located on the upper arm on the peripheral side of the tourniquet 54. In still another aspect, the planned puncture site SP may be located on a lower limb and the tourniquet 54 may be wrapped around the lower limb on the central side of the planned puncture site SP.

Figure 5:
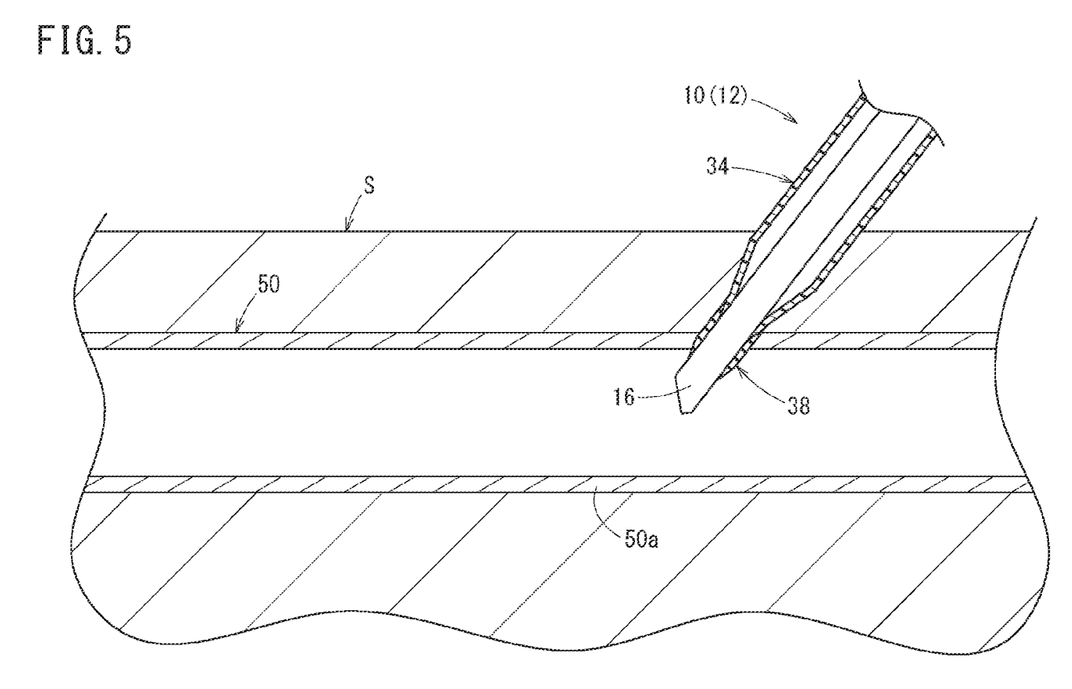
FIG. 5 is a second explanatory view of the procedure using the catheter assembly.

After wrapping the tourniquet 54 in this manner, the puncturing operation is performed. In the puncturing operation, a user (a doctor, a nurse, or the like) presses the distal portion of the catheter assembly 10 against the patient while gripping the housing 24 illustrated in FIG. 1, thereby puncturing a skin S toward a puncture target blood vessel 50. As a result, the skin S is punctured with the distal portions of the inner needle 16 and the catheter 12 as illustrated in FIG. 5 (a puncture step).

Next, the user operates the catheter operation member 20 in the distal direction to advance the catheter member 17 (the catheter 12 and the catheter hub 14) to the central side while fixing the position of the needle hub 18 (the housing 24) illustrated in FIG. 1 (a catheter advance step). Then, the catheter 12 is inserted to a target position in the blood vessel. At that time, the flexible portion 38 of the catheter 12 is caused to pass through a portion 50n, which becomes narrower as compared with the time when the tourniquet 54 is not wrapped or collapses due to the tourniquet 54 wrapped around a part of the human body, of the blood vessel 50 as illustrated in FIG. 4 (a passage step). In FIG. 4, the catheter 12 is illustrated by an imaginary line.

Next, the user pulls the housing 24 in the proximal direction while holding the positions of the catheter operation member 20 and the catheter member 17 illustrated in FIG. 1. Accordingly, the catheter member 17 and the catheter operation member 20 completely come out of the housing 24, and the inner needle 16 is removed from the catheter 12 in the proximal direction.

Next, the catheter operation member 20 is detached from the catheter hub 14. Accordingly, the catheter member 17 is indwelled in the patient. Incidentally, the catheter operation member 20 may be kept attached to the catheter hub 14 depending on a preference of the user.

Next, the connector of the infusion tube (not illustrated) is connected to the proximal side (the proximal portion of the catheter hub 14) of the catheter member 17 from which the inner needle 16 has been removed, and the infusion solution (medicinal liquid) is administered from the infusion tube to the patient.

In this case, the catheter assembly 10 according to the present embodiment has the following effects.

According to the catheter assembly 10, the flexible portion 38, which is more flexible than the catheter body 34, is provided at the distal portion of the catheter body 34 as illustrated in FIG. 2. Thus, it is possible to prevent the distal end of the catheter 12 from being caught by a blood vessel back wall 50a, which is a blood vessel wall of the blood vessel 50 on the opposite side of a puncture spot at the time of advancing the catheter 12 to insert the catheter 12 into the blood vessel 50 after puncturing a skin S with the distal portion of the catheter assembly 10 even when a puncture angle, which is an angle between a central axis of the blood vessel 50 to be punctured and a central axis of the inner needle 16 with which the puncture is performed, is large as illustrated in FIG. 6.

Figure 6:
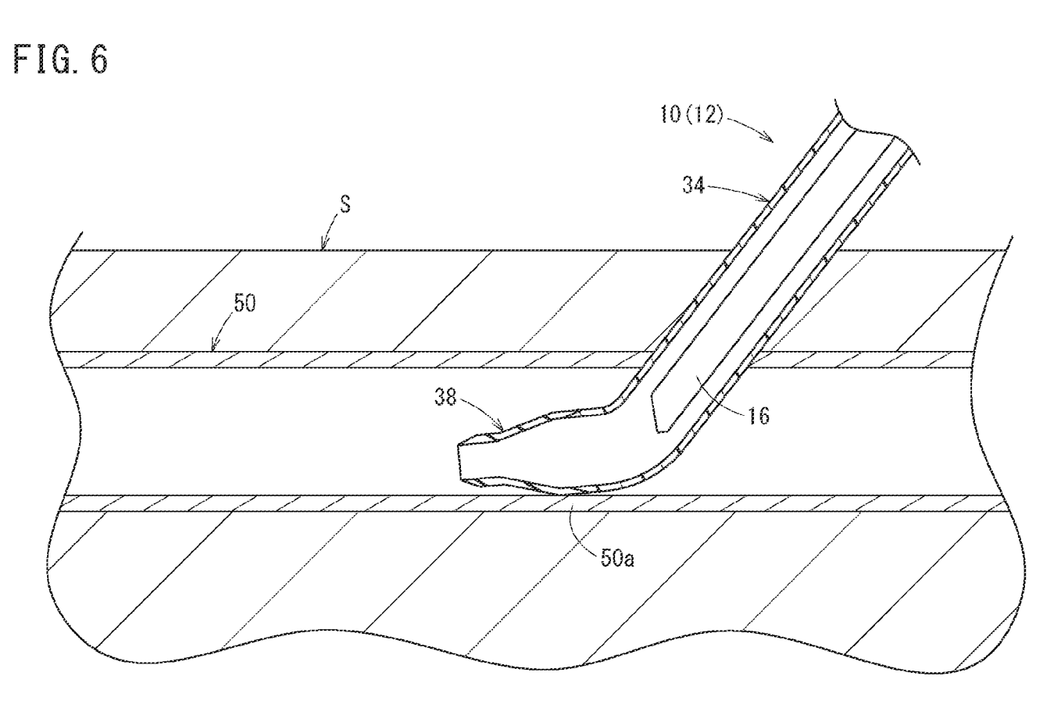
FIG. 6 is a third explanatory view of the procedure using the catheter assembly.

That is, the flexible portion 38 is brought into contact with the blood vessel back wall 50a and is pressed by the blood vessel back wall 50a to be easily deformed at the time of advancing the catheter 12 as illustrated in FIG. 6, and thus, it is possible to prevent the distal end of catheter 12 from being caught by the blood vessel back wall 50a. As a result, it is possible to prevent the catheter 12 from being hardly inserted into the blood vessel 50 or to prevent the blood vessel back wall 50a from being damaged by the distal end of the catheter 12.

Because the change in flexibility of the second material between 25° C. and 37° C. forming the flexible portion 38 is smaller than the change in flexibility of the first material between 25° C. and 37° C. forming the catheter body 34, the distal end of the catheter 12 is relatively soft, and thus, hardly damages the blood vessel 50, and the catheter body 34 is relatively hard, and thus, is easily inserted when the catheter 12 is inserted into the living body. After the catheter 12 indwells, the flexible portion 38 constituting the distal end of the catheter 12 is not such soft as compared with the time of insertion, and thus, the flexible portion 38 is hardly crushed during blood suction. On the other hand, after the catheter 12 indwells, the catheter body 34 softens due to the human body temperature as compared with the time of insertion and adapts to a shape of the blood vessel 50 (which is not linear but has some curvature in general), and thus, the stimulation to the blood vessel 50 is reduced. Thus, it is possible to reduce the discomfort given to the patient while the catheter 12 indwells, the occurrence of phlebitis, and the occurrence of extravasation.

As illustrated in FIG. 2, the flashback flow path 32 is formed between the catheter 12 and the inner needle 16, and the inner needle 16 is provided with the introduction path 44 that communicates with the flashback flow path 32 to introduce blood into the flashback flow path 32. The proximal end 44a of the introduction path 44 is provided on the proximal side of the axial center position Pc of the portion of the flexible portion 38 present on the distal side of the distal-most portion of the catheter body 34. In addition, the catheter 12 has the close contact portion 30 in which at least a part of the inner circumferential surface is in close contact with the outer circumferential surface of the inner needle 16, and at least the proximal end 44a of the introduction path 44 is provided on the proximal side of the close contact portion 30.

With the above configuration, it is possible to prevent the flexible portion 38 from being deformed to block the introduction path 44 at the time of puncture, and thus, it is possible to easily confirm the flashback of blood.

In the close contact portion 30, both the flexible portion 38 and the catheter body 34 are in close contact with the inner needle 16. With this configuration, an appropriate fitting force between the inner needle 16 and the catheter 12 can be obtained. With the appropriate fitting force, the flexible portion 38 is prevented from being curled, and the inner needle 16 can be easily removed from the catheter 12 at the time of puncturing the skin.

Figure 7:
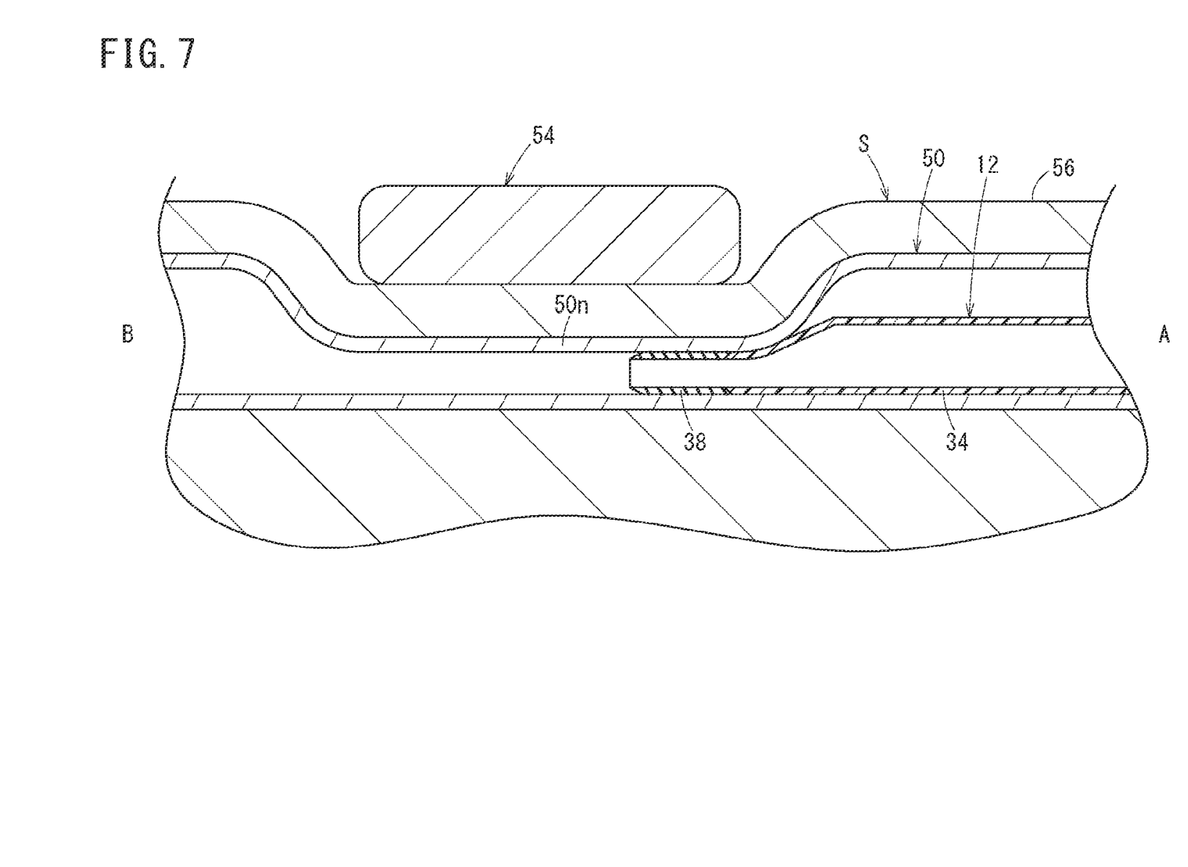
FIG. 7 is a fourth explanatory view of the procedure using the catheter assembly.

In the above-described method for inserting the catheter assembly 10, the catheter 12 is advanced with the tourniquet 54 wrapped as illustrated by the imaginary line in FIG. 4, and thus, it is possible to prevent the catheter 12 from falling off due to vasoconstriction that occurs when the tourniquet 54 is removed. Because the flexible portion 38 is provided at the distal end of the catheter 12, the flexible portion 38 is easily deformed and easily enters the narrowed portion 50n of the blood vessel 50 when the catheter 12 passes from a peripheral side A to a central side B through the blood vessel 50 (portion 50n) narrowed by the tourniquet 54 as illustrated in FIG. 7. As a result, the catheter 12 can easily pass through the portion 50n of the blood vessel 50 narrowed by the tourniquet 54, and damage to the blood vessel 50 accompanying the passage of the catheter 12 can be suppressed.

From the above description, the following invention (method for inserting the catheter assembly) can be grasped.

A method for inserting a catheter assembly including:
preparing a catheter assembly that includes a catheter and an inner needle inserted through the catheter, the catheter having a catheter body and a flexible portion that is provided on a distal portion of the catheter body, includes a distal-most portion of the catheter, and is more flexible than the catheter body;
wrapping a tourniquet around a part of a human body on a central side of a planned puncture site;
puncturing a blood vessel at the planned puncture site in the part of the human body with the inner needle of the catheter assembly;
advancing the catheter into the blood vessel; and
causing the flexible portion to pass through a portion, which becomes narrower as compared with a time when the tourniquet is not wrapped or collapses due to the tourniquet wrapped around the part of the human body, of the blood vessel.

Figure 8:
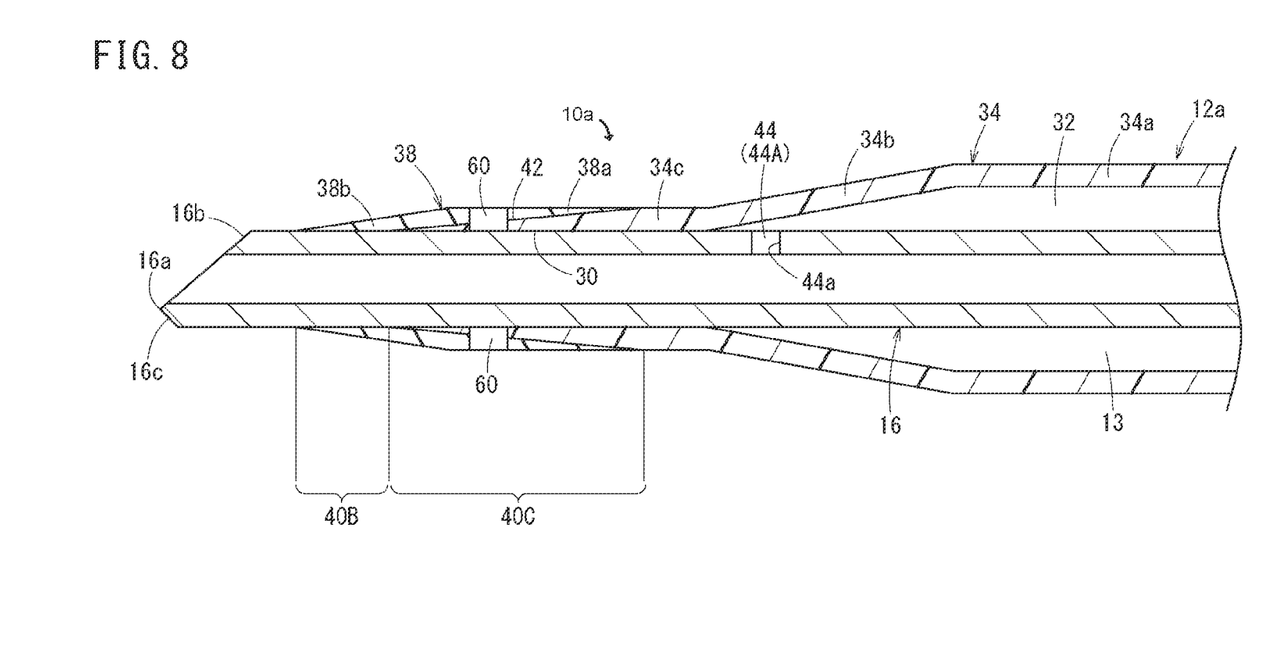
FIG. 8 is a cross-sectional view of a distal portion of a catheter assembly having another configuration.

In a catheter assembly 10a illustrated in FIG. 8, a catheter 12a is provided with a side hole 60 that is open in the close contact portion 30. The catheter 12a is configured in the same manner as the catheter 12 (FIG. 1 and the like) except that the side hole 60 is provided. A plurality of the side holes 60 are provided at intervals in the circumferential direction. The side hole 60 is provided on the distal side of the most proximal position of the close contact portion 30. The side hole 60 penetrates from an inner circumferential surface to an outer circumferential surface of the catheter 12a. The side hole 60 penetrates through both the catheter body 34 and the flexible portion 38.

In another aspect, only the single side hole 60 may be provided in the circumferential direction. The plurality of side holes 60 may be provided at intervals in the axial direction of the catheter 12a. The side hole 60 may penetrate through only one of the catheter body 34 and the flexible portion 38. On the inner circumferential surface of the catheter 12a, the side hole 60 may be provided to straddle both the catheter body 34 and the flexible portion 38. The side hole 60 may be inclined with respect to the radial direction of the catheter 12a. When the groove portion 44B as illustrated in FIG. 3 is adopted as the introduction path 44 in the catheter 12a, it is preferable that the side hole 60 of the catheter 12a be displaced from the groove portion 44B in the circumferential direction.

Figure 9A:
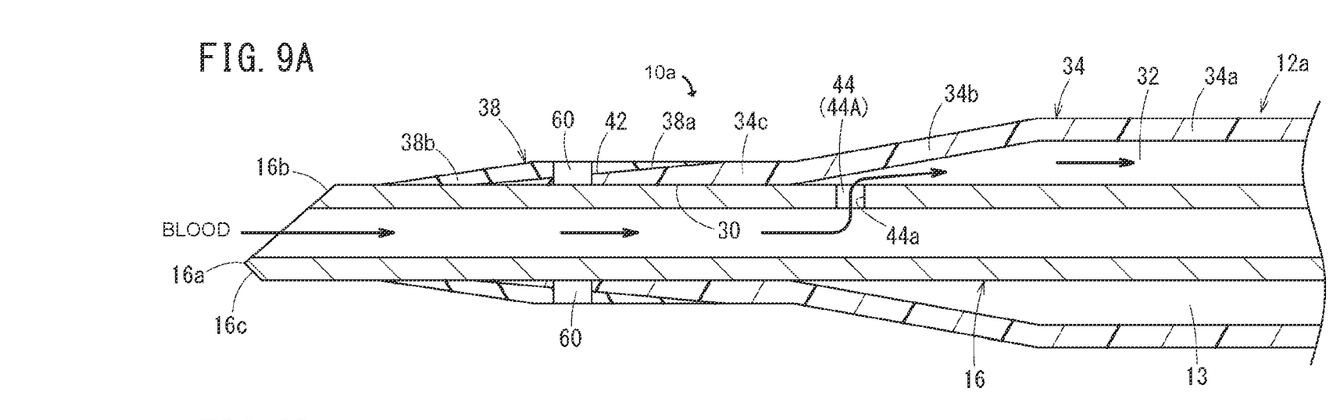
FIG. 9A is an explanatory view of first action of the catheter assembly illustrated in FIG. 8.

In the use of the catheter assembly 10a configured as described above, blood flows into the flashback flow path 32 via the lumen of the inner needle 16 and the introduction path 44 as the blood vessel 50 is punctured with the catheter assembly 10a as illustrated in FIG. 9A. Although the catheter 12a is provided with the side hole 60, and the side hole 60 is open in the close contact portion 30 and is not open in the flashback flow path 32, and thus, the blood does not leak out of the catheter 12a from the flashback flow path 32 through the side hole 60.

In addition, the catheter 12a is provided with the side hole 60 that is open in the mixed region 40C in the catheter assembly 10a illustrated in FIG. 8. Because the mixed region 40C includes the catheter body 34, and thus, is relatively harder than the single flexible portion region 40B.

With the above configuration, it is possible to suppress the deformation of the catheter 12a during suction and prevent the blockage of the catheter 12a as compared with the case where the side hole 60 is provided in the single flexible portion region 40B.

Figure 9B:
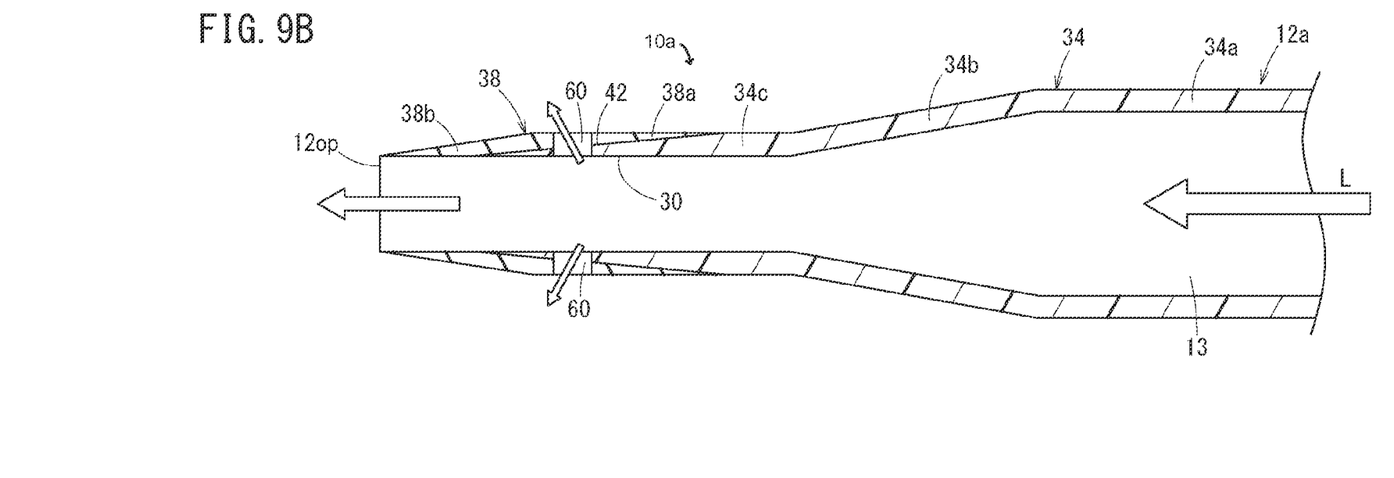
FIG. 9B is an explanatory view of second action of the catheter assembly illustrated in FIG. 8.

When a liquid L, such as a contrast agent, is introduced into the blood vessel at high pressure into the catheter 12a after removing the inner needle 16 from the catheter 12a as illustrated in FIG. 9B, the liquid L is ejected not only from a distal opening 12op of the catheter 12a but also from the side hole 60. Thus, as the pressure of the ejection of the liquid L disperses, it is possible to prevent the high pressure from acting locally on the blood vessel 50 and reduce the influence on the blood vessel 50. In addition, it is possible to prevent the position of the catheter 12a from being displaced due to the reaction of the ejection of the liquid L.

Incidentally, the following invention (catheter assembly) can be grasped in relation to the configuration illustrated in FIG. 8.

A catheter assembly including:
a catheter; and
an inner needle inserted through the catheter,
in which the catheter has a catheter body and a flexible portion which is provided on a distal portion of the catheter body, includes a distal-most portion of the catheter, and is more flexible than the catheter body,
the catheter has a close contact portion in which at least a part of an inner circumferential surface is in close contact with an outer circumferential surface of the inner needle, both the flexible portion and the catheter body being in close contact with the inner needle in the close contact portion,
the catheter is provided with a side hole that is open in the close contact portion,
a flow path for flashback confirmation is formed between the catheter and the inner needle, and
the inner needle is provided with an introduction path that communicates with the flow path and introduces blood into the flow path.

In the present embodiment, the physical properties of the first material forming the catheter body 34 and the second material forming the flexible portion 38 in the catheter assembly 10a illustrated in FIG. 8 are not limited to the above-described combination. For example, the change in flexibility of the second material between 25° C. and 37° C. may be the same as or larger than the change in flexibility of the first material between 25° C. and 37° C.

The present invention is not limited to the above-described embodiment, and various modifications can be made without departing from a gist of the present invention.

What is claimed is:

1. A catheter assembly comprising:
a catheter; and
an inner needle inserted through the catheter, wherein:
the catheter comprises:
  a catheter body that is made of a first material, and
  a flexible portion that is located on a distal portion of the catheter body, includes a distal-most portion of the catheter, is more flexible than the catheter body, and is made of a second material, and
where the elastic modulus of the first material at 25° C. is H1a, the elastic modulus of the first material at 37° C. is H1b, the elastic modulus of the second material at 25° C. is H2a, and the elastic modulus of the second material at 37° C. is H2b,
H2a/H2b<H1a/H1b.

2. The catheter assembly according to claim 1, wherein:
a flow path for flashback confirmation is located between the catheter and the inner needle,
the inner needle comprises an introduction path that communicates with the flow path to introduce blood into the flow path,
part of the flexible portion is located on a distal side of a distal-most portion of the catheter body, and
a proximal end of the introduction path is located on a proximal side of an axial center position of said part of the flexible portion.

3. The catheter assembly according to claim 1, wherein:
the catheter has a close contact portion where at least a part of an inner circumferential surface of the catheter is in close contact with an outer circumferential surface of the inner needle, and
both the flexible portion and the catheter body are in close contact with the inner needle at the close contact portion.

4. The catheter assembly according to claim 3, wherein:
the catheter comprises a side hole at the close contact portion.

5. A catheter assembly comprising:
a catheter hub;
a catheter fixed to the catheter hub;
a needle hub;
an inner needle fixed to the needle hub and inserted through the catheter; and
a catheter operation member mounted to the catheter hub, wherein:
the catheter comprises:
  a catheter body that is made of a first material, and
  a flexible portion that is located on a distal portion of the catheter body, includes a distal-most portion of the catheter, is more flexible than the catheter body, and is made of a second material, and
where the elastic modulus of the first material at 25° C. is H1a, the elastic modulus of the first material at 37° C. is H1b, the elastic modulus of the second material at 25° C. is H2a, and the elastic modulus of the second material at 37° C. is H2b,
H2a/H2b<H1a/H1b.

6. The catheter assembly according to claim 5, wherein:
a flow path for flashback confirmation is located between the catheter and the inner needle,
the inner needle comprises an introduction path that communicates with the flow path to introduce blood into the flow path,
part of the flexible portion is located on a distal side of a distal-most portion of the catheter body, and
a proximal end of the introduction path is located on a proximal side of an axial center position of said part of the flexible portion.

7. The catheter assembly according to claim 5, wherein:
the catheter has a close contact portion where at least a part of an inner circumferential surface of the catheter is in close contact with an outer circumferential surface of the inner needle, and
both the flexible portion and the catheter body are in close contact with the inner needle at the close contact portion.

8. The catheter assembly according to claim 7, wherein:
the catheter comprises a side hole at the close contact portion.

9. A catheter assembly comprising:
a catheter; and
an inner needle inserted through the catheter, wherein:
the catheter comprises:
  a catheter body that is made of a first material comprising a fluorine-based resin, an olefin-based resin, polyurethane, polyester, polyamide, a polyether nylon resin, or a mixture of an olefin-based resin and an ethylene-vinyl acetate copolymer, and
  a flexible portion that is located on a distal portion of the catheter body, includes a distal-most portion of the catheter, is more flexible than the catheter body, and is made of a second material comprising a rubber material or a thermoplastic elastomer material, and where the elastic modulus of the first material at 25° C. is H1a, the elastic modulus of the first material at 37° C. is H1b, the elastic modulus of the second material at 25° C. is H2a, and the elastic modulus of the second material at 37° C. is H2b, H2a/H2b<H1a/H1b.

10. The catheter assembly of claim 9, wherein the first material is polytetrafluoroethylene (PTFE), ethylene-tetrafluoroethylene copolymer (ETFE), or perfluoroalkoxy fluorine resin (PFA).

11. The catheter assembly of claim 9, wherein the first material is polyethylene, polypropylene, or a mixture thereof.

12. The catheter assembly of claim 9, wherein the second material is natural rubber, butyl rubber, isoprene rubber, butadiene rubber, styrene-butadiene rubber, or silicone rubber.

13. The catheter assembly of claim 9, wherein the second material is polyurethane thermoplastic elastomer, polyester thermoplastic elastomer, polyamide thermoplastic elastomer, olefin thermoplastic elastomer, styrene thermoplastic elastomer, or a mixture thereof.

14. The catheter assembly according to claim 9, wherein:
a flow path for flashback confirmation is located between the catheter and the inner needle,
the inner needle comprises an introduction path that communicates with the flow path to introduce blood into the flow path,
part of the flexible portion is located on a distal side of a distal-most portion of the catheter body, and
a proximal end of the introduction path is located on a proximal side of an axial center position of said part of the flexible portion.

15. The catheter assembly according to claim 9, wherein:
the catheter has a close contact portion where at least a part of an inner circumferential surface of the catheter is in close contact with an outer circumferential surface of the inner needle, and
both the flexible portion and the catheter body are in close contact with the inner needle at the close contact portion.

16. The catheter assembly according to claim 15, wherein:
the catheter comprises a side hole at the close contact portion.

* * * * *